(12) United States Patent
Moshenyat et al.

(10) Patent No.: US 7,097,860 B2
(45) Date of Patent: Aug. 29, 2006

(54) METHOD AND COMPOSITION FOR TREATMENT OF INFLAMMATORY AND INFLAMMATION-RELATED DISORDERS

(76) Inventors: Aaron Moshenyat, 490 NW. 20th St., Apt 206, Boca Raton, FL (US) 33421; Anna Moshenyat, 490 NW. 20th St., Apt 206, Boca Raton, FL (US) 33421; Reuven Moshenyat, 4611 12 Ave. Apt 2J, New York City, NY (US) 11219; Yitzchak Moshenyat, 4611 12 Ave., Apt 2J, New York City, NY (US) 11219

( * ) Notice: Subject to any disclaimer, the term of this patent is extended or adjusted under 35 U.S.C. 154(b) by 97 days.

(21) Appl. No.: 10/146,735

(22) Filed: May 16, 2002

(65) Prior Publication Data

US 2003/0026853 A1 Feb. 6, 2003

Related U.S. Application Data

(63) Continuation-in-part of application No. 09/921,965, filed on Aug. 3, 2001, now abandoned.

(51) Int. Cl.
| | | |
|---|---|---|
| A61K 33/06 | (2006.01) | |
| A61K 33/08 | (2006.01) | |
| A61K 33/10 | (2006.01) | |
| A61K 33/12 | (2006.01) | |
| A61K 33/14 | (2006.01) | |
| A61K 33/04 | (2006.01) | |
| A61P 29/00 | (2006.01) | |
| A61P 1/00 | (2006.01) | |
| A61P 3/10 | (2006.01) | |
| A61P 15/00 | (2006.01) | |
| A61P 19/02 | (2006.01) | |

(52) U.S. Cl. ............ 424/697; 424/681; 424/682; 424/683; 424/686; 424/688; 424/689; 424/692; 514/244; 514/246; 514/870; 514/871; 514/886; 514/887; 514/894; 514/925

(58) Field of Classification Search ........ 424/681–683, 424/686, 692, 697, 722, 688, 689; 514/244, 514/246, 825, 826, 829–831, 858–867, 870, 514/871, 886–888, 894, 925–928
See application file for complete search history.

(56) References Cited

U.S. PATENT DOCUMENTS 5,466,680 A * 11/1995 Rudy .................. 514/57

FOREIGN PATENT DOCUMENTS

| WO | 95/31991 | * 11/1995 |
| WO | 96/19182 | * 6/1996 |

OTHER PUBLICATIONS

Chemical Abstracts 31:28353 (1937).*
Medline Abstract, accession No. 83231318 (1983).*
Sameshima, H. et al., "Pretreatment with magnesium sulfate protects against hypoxic-ischemic brain injury . . ." American Journal of Obstetrics and Gynecology, vol. 180, No. 3, Part 1, Mar. 1999, pp. 725-730.*
Drug Facts and Comparisons, Facts and Comparisons, St. Louis, 1999, pp. 149-151.*
Chemical Abstracts 134:85 (2000).*
Mutschler, E. et al. Drug Actions. CRC PRess, Boca Raton (FL), 1995, pp. 6-8.*
Medline abstract, accession No. 88287547 (1988).*
Chemical Abstracts 135:41946 (2001).*
Chemical Abstracts 116:38631 (1991).*
Medline abstract 2005280148 (2005).*
Medline abstract 97043986 (1997).*
Medline abstract 97404718 (1997).*
Medline abstract 97225055 (1997).*
Medline abstract 1999352508 (1999).*

* cited by examiner

*Primary Examiner*—John Pak
(74) *Attorney, Agent, or Firm*—John C. Smith

(57) ABSTRACT

A method of reducing inflammation in a variety of disorders by using an intraperitoneal solution of magnesium. The solution can be used for treating inflammatory and inflammation-related disorders in animals and/or humans. Application of the solution reduces inflammation and thereby assists in the healing process. An alternative method involves the intraperitoneal administration of a solution containing magnesium salts. Another alternative method provides for treatment of inflammatory and inflammation-related disorders in animals by way of intraperitoneal administration of a solution containing magnesium salts, methenamine or its salts and dextrose. The method further provides the use of methenamine or its salts and/or dextrose in combination with magnesium.

23 Claims, No Drawings

METHOD AND COMPOSITION FOR TREATMENT OF INFLAMMATORY AND INFLAMMATION-RELATED DISORDERS

BACKGROUND OF THE INVENTION

Cross-Reference to Related Applications

This non-provisional patent application is a continuation in part of the commonly owned co-pending application entitled "Peritoneal Solution for Treating Animals with Gynecological, Obstetrical, Inferility, Gastrointestinal, Skin, Muscular and Bone Diseases, and Metabolic Disturbances", filed Aug. 3, 2001, bearing U.S. Ser. No. 09/921,965, now abandoned and naming Aaron Moshenyat, Anna Moshenyat, Reuven Moshenyat, and Yitzchak Moshenyat, the named inventors herein, as sole inventors, the contents of which is specifically incorporated by reference herein in its entirety.

1. Technical Field

The present invention relates to the treatment of inflammatory and inflammation-related disorders of both animals and human beings. In particular, it relates to a method of using an intraperitoneal solution of magnesium salts for treatment of inflammatory and inflammation-related disorders in animals and/or humans, and the use of methenamine or its salts and/or dextrose in combination with the magnesium salt solution.

2. Background Art

The living organism is an ideally formed system that comprises all mechanisms of autoregulation for its long existence. Functions of the endocrine, the immune, and the central nervous systems share a common method of energy formation through the mechanisms of combining phosphorus groups of ATP ("Adenosine Triphosphate"), ADP ("Adenosine Diphosphate"), AMP ("Adenosine Monophosphate") with magnesium. This process serves as a key component in the formation of free energy. An abundance of magnesium is necessary for these reactions to take place. Alternatively, a magnesium deficiency can result in pathological processes. One such process is inflammation exacerbated by magnesium deficiency. A wide variety of medical conditions in humans and/or animals causes inflammation, which in turn can interfere with treatment and recovery. It would be desirable to have a method of increasing the amount of available magnesium to enhance an assist the creation of free energy in sufficient amounts to suppress or ameliorate the pathological process.

While recognizing the need for a magnesium in living organisms, the prior art has failed to provide a method of providing additional magnesium to organisms in a safe, effective, and inexpensive manner.

SUMMARY OF THE INVENTION

The present invention solves the foregoing problems by providing an intraperitoneal solution of magnesium salts for treatment of inflammatory and inflammation-related disorders in animals and/or humans, and the use of methenamine or its salts and/or dextrose in combination with the magnesium salt solution. The solution is used as a treatment of inflammatory and inflammatory-related disorders by using a pharmaceutical composition of magnesium salts, methenamine or its salts, and dextrose which is administered as an intraperitoneal solution in an amount effective to treat and to relieve symptoms of inflammation for the particular living organism in question.

DESCRIPTION OF THE PREFERRED EMBODIMENT

Prior to a detailed description of the invention, a general overview of the invention will be presented. The present invention is a method of treating inflammation with a magnesium salt based pharmaceutical solution that provides necessary materials to the body to assist it in the healing process. Knowledge of inflammation is essential to understand the process by which magnesium works in the present invention. The process that takes place in the pathogenesis of inflammation is a characteristic of a related series of events and processes initiated by bacterial, viral or mycotic antigen.

The sequence of events in the inflammatory process is as follows: first, an antigen is absorbed and processed by an antigen-presenting cell and then presented to T cells, and as a result, the T cells are activated. Once the T cells are activated, they produce INF-γ ("Interferone Gamma") which in turn leads to activation of macrophages. As used herein, the prefix "IL" is used to describe "Interleukine." The activated macrophages produce IL-12 and IL-18 that activate Th1 ("T helper cells 1") cells to produce IL-1, IL-8, and TNF ("Tumor Necrosis Factor"). The TNF has a broad spectrum of pro-inflammatory effects which induces expression of adhesion molecules by vascular endothelium, permitting the influx of newly recruited inflammatory cells into the mucosa. A critical step in the creation of the inflammatory response is the recruitment of inflammatory cells from systemic circulation. The "intercellular adhesion molecule" ICAM-1 that is produced on the endothelium mainly binds monocytes and neutrophils. Leukocytes then migrate along the gradient of chemoattractants into the submucosa and mucosa. Once present, these cells produce numerous inflammatory substances. Chief among these inflammatory substances are products of arachidonic acid metabolism, tromboxanes, leukotriens, prostaglandins, and free radicals, including reactive oxygen metabolites and nitric oxide.

One of these inflammatory substances, Leukotriens, are produced by a variety of cell types, including cells of the lung, connective tissue, smooth muscle, macrophages, mast cells and monocytes. Leukotriens act indirectly by promoting the release of IFN from T lymphocytes. Once released, the IFN activates macrophages to release IL-1 and TNF, increases class I and II MHC production, increases NK ("Natural Killer") activity, and increases monocyte 1L-2 receptors. When the IL-1 is released, it promotes T-cell proliferation and stimulates acute-phase protein synthesis. IL-2 is the T cell growth factor, co-stimulates B cell growth and differentiation. Il-6 induces acute-phase protein synthesis, promotes T-cell activation and IL-2 production, and it also stimulates B cells to secrete immunoglobulins and serves as a colony stimulating factor. As a result of the inflammatory process, the humoral and T-cell mediated immune responses are activated, which allow the organism to repair tissue damage and defend itself against infection.

The presence of magnesium in a living body is known in the arts. Magnesium is a widely distributed alkali metal. It ranks fourth among the cations in abundance in mammals. However, in spite of its prominence as a body constituent, it has received surprisingly little attention in either nutrition or medicine. In fact, methods of providing additional magnesium to living organisms for the purpose of reducing the effects of inflammation, and thereby assisting the healing process, has received little attention by those skilled in the arts.

Magnesium serves as a cofactor for more than three hundred reactions that are related to the transfer of phosphate groups. It is essential in all reactions involving ATP, its hydrolysis to ADP and AMP as well as the synthesis of ATP. It is involved in every step related to the replication and transcription of DNA and the translation of mRNA. During the translation of the mRNA, the ribosomes are stabilized with the help of magnesium and are able to dissociate to subunits if the concentration of the magnesium is low and the process of the cell synthesis stops.

Nearly all the glycolytic enzymes require $Mg^{2+}$ for activity. Since $Mg^{2+}$ forms complexes with the phosphate groups of the glycolytic intermediates and of ADP and ATP, the substrate binding sites of many of the glycolytic enzymes appear to be specific for the $Mg^{2+}$ complexes of the phosphorylated intermediates. The ATP-ADP system functions as a carrier of chemical energy because ADP is able to accept a phosphate group during coupled energy-yielding reactions of catabolism and the ATP so formed is able to donate its terminal phosphate group in coupled energy-requiring reactions.

ATP was first isolated from acid extracts of muscle. Its structure was originally deduced by degradation experiments and subsequently confirmed by total chemical synthesis. It is further believed that ATP serves as a principal means of transferring chemical energy in the cell. At pH 7.0, both ATP and ADP are highly charged anions. ATP has four ionizable protons in its triphosphoric acid group. Three have low pK' values of about 2 to 3 and are thus completely dissociated at pH 7.0; the fourth has a pK' of 6.50 and therefore is about 75 percent dissociated at pH 7.0. ADP has three ionizable protons; two are completely dissociated at pH 7.0 and the third, which has a pK' of 7.2, is about 39 percent dissociated at pH 7.0. The high concentration of negative charges around the triphosphate group of ATP is an important factor in its high-energy nature. In the intact cell, very little ATP and ADP exist as free anions; they are largely present as the 1:1 $MgATP_2$- and MgADP- complexes, because of the high affinity of the pyrophosphate group for binding divalent cations and the high concentration of $Mg^{2+}$ in intracellular fluid. In most enzymatic reactions in which ATP participates as phosphate donor, its active form is the $MgATP_2$- complex. Free ATP, ADP, and phosphate form complexes with $Mg^{2+}$ by reversible reactions: $Mg^{2+}+ATP_{4-}=MgATP_2-$; $Mg^{2+}+ADP_{3-}=MgADP-$; $Mg^{2+}+HPO4_{2-}=MgHPO4$. Therefore, during the inflammatory process, an abundance of magnesium is necessary to produce free energy and to increase the function of the immune system to fight the bacterial, viral and mycotic pathogens. An advantage of the invention provided herein is that it provides an abundance of magnesium for use by the body in the healing process.

Mitochondria are the powerhouse of the cell in which the process of oxidation takes place. The energy that is necessary for the cells activity comes from the hydrolysis of the phosphate related elements such as ATP. The creation of energy and the synthesis of ATP take place in the mitochondrias by the process of phosphorylation. The number of oxidation-phosphorylation reactions that take place in a living organism are used not only for the biosynthesis of many elements but also for detoxification of many toxins which are formed during the cell's life and death. Any process that inhibits the process of oxidation-phosphorylation, mainly lack of energy, will lead to biological dysfunction and the formation of biological changes.

Repair of injured epithelium is accomplished by the participation of a variety of growth factors such as EGF (Epithelial Growth Factor), TGF-β (Tumor Growth Factor-b), PDGF (Prostaglandin Derived Growth Factor) and short-chain fatty acids. The activity of many enzymes, membrane channels, and other target proteins is regulated by phosphorylation. The enzymes catalyzing these reactions are called protein kinases. The terminal (y) phosphoryl group of ATP is transferred to specific serine and threonine residues by one class of protein kinases and to specific tyrosine residues by another. The acceptors in protein phosphorylation reactions are located inside the cells, where ATP is abundant.

The process of phosphorylation plays an important role in the process of inflammation during the healing phase when growth factors such as TGF-β, PDGF and Epithelial Growth Factors bind to cellular receptors which cause their autophosphorylation. The process of autophosphorylation involves the phosphorylation of tyrosine kinase, which induces the transmission of growth signals. EGF receptor is a single polypeptide chain consisting of 1186 residues. The receptor is enzymatically inactive in the absence of growth factor. Binding of EGF to the extracellular domain causes the receptor to dimerize and undergo autophosphorylation. The catalytic site of one chain phosphorylates five tyrosine kinases located near the C terminus of the other chain in the dimmer. Autophosphrylation enhances the capacity of the receptor to phosphorylate other targets. Phosphorylated tyrosines generally serve as docking sites for SH2 domains that are present in numerous signaling proteins. The binding of platelet-derived growth factor and fibroblast growth likewise dimerizes their receptors and leads to their autophosphorylation. As it appears, kinase activity is essential for the transmission of growth signals. Having looked at the underlying processes which require magnesium, we now turn to a detailed discussion of how the invention provides sufficient magnesium to assist in the aforedescribed processes.

The normal range for magnesium in serum is 1.3–2.1 meq/l. The biggest problem is that its therapeutic level is close to the toxic level. In order to provide the benefits of the invention, a method had to be developed to provide an abundance of magnesium without the exceeding toxic levels. This problem was solved by using an intraperitoneal solution of magnesium. The intraperitoneal solution is processed through the liver which creates the abundance of $Mg^{2+}$ necessary for the production of free energy. The intraperitoneal administration allows amounts of magnesium salts to be safely administered intraperitoneally which would be toxic if administered via IV or IM. The reason for this is that it avoids the situation in which it would bypass the liver and pass directly to other organs, such as the brain or heart as would be the case if injected into muscle tissue or given via IV. As a result, the magnesium increases the function of the immune system while avoiding toxic levels despite the dosage amounts. The peritoneal cavity offers a large absorbing surface from which drugs enter the circulation rapidly, but primarily by way of the portal vein; first-pass hepatic losses are thus possible. The phenomenon known as the first-pass effect allows the drugs that reach the hepatic circulation to reduce their concentration in the blood stream and also reduce their toxicity. Most liver cells (hepatocytes) contain many complex and active systems that metabolize drugs. Drug-metabolizing reactions are often referred to as detoxification reactions, which implies that all drugs are metabolized to less active and therefore less toxic compounds.

Another aspect of the present invention is to provide methenamine (hexamethylenetetramine, $C_6H_{12}N_4$), or its salts, and dextrose ($C_6H_{12}O_6H_2O$), which are used in combination with magnesium in treatment of inflammatory disorders. Methenamine has several characteristics: methenamine comes as a crystalline powder of white color; it is flammable; the powder is very soluble in water, and when in solution, it exists as an alkaloid; and it is not resistant to boiling. The solution is made by antiseptic techniques. Methenamine is a synthetic antibacterial agent that is chemically unrelated to other currently available anti-infectives. Methenamine is hydrolyzed by acids to formaldehyde and ammonia. The antibacterial effect of methenamine is dependent upon the release of formaldehyde from the drug in the acidic medium when urine pH is 5.5 or less. It is known that methenamine breaks down to formaldehyde. This process occurs not only in kidneys but also in areas of inflammation because, during the process of inflammation, the medium is acidic.

It is known that Formaldehyde is a nonspecific antibacterial agent. Because it is non-specific, it does not lead to the development of resistance to gram-positive and gram-negative bacteria when methenamine is used for prolonged periods. Formaldehyde is effective against a variety of bacteria such as *Enterobacter, Enterococcus faecalis, Escherrichia coli, Klebsiella, Proteus, Pseudomonas aeruginosa, Staphylococcus aureus,* and *S. epidermididis,* among others.

Methenamine is used for prophylaxis or suppression of recurrent urinary tract infections, especially when long-term therapy is considered necessary. Methenamine and its salts are not effective in systemic bacterial infections and have no effect on bacteria in blood or tissues outside the urinary tract. However, it is known that methenamine can be used in urinary tract infections because the urinary tract is acidic and the methenamine breaks down in acidic areas. Likewise, methenamine is effective in areas of inflammation because the media is acidic in those inflamed areas. It can also be used in the treatment of bronchitis, arthritis, hepatitis, and other infectious and noninfectious diseases, because it increases membrane permeability, which helps to eliminate the toxic materials from the body. Further, methenamine has been used for encephalitis, meningitis, and keratitis.

Limited information is available on the acute toxicity of methenamine and its salts. Methenamine hippurate has been administered to monkeys from six months old with double the normal dose without adverse effects. Dogs and rats have received up to 600 mg/kg of methenamine administered via IV in a single dose without evidence of toxic effects. Reproduction studies in rats and rabbits using methamine have not revealed evidence of harm to the fetus. Although safe use of methenamine or its salts during pregnancy has not been definitely established, the drugs have been used in pregnant women without adverse effects to the fetus.

A third component of invention is dextrose (D-glucose). Dextrose comes as a crystal powder with a sweet taste, easily dissolvable in water. It is resistant to boiling. The solution can be sterilized at 110 degrees of Celsius during a forty minutes period. Dextrose works on the receptors of the blood vessels and other tissues via the central nervous system, and increases the function of the cells and tissues by providing free energy to the cells. The isotonic solution of dextrose brings about the stimulation of the cellular functions. Also, dextrose with the combination of any substance lowers its toxicity and increases its duration.

Complex organic molecules, such as glucose, contain much potential energy because of their high degree of structural order; they have relatively little randomness, or entropy. When the glucose molecule is oxidized by molecular oxygen to form six molecules of $CO_2$ and six of water, its atoms undergo an increase in randomness; they become separated from each other and may assume many different locations in relation to each other. As a result of this transformation, the glucose molecule undergoes a loss of free energy, which is useful energy capable of doing work at constant temperature and pressure. The free energy of glucose is harnessed by the cell to do work. The free energy of cellular fuels is conserved as chemical energy, specifically the phosphate-bond energy of adenosine triphosphate (ATP). ATP is enzymatically generated from adenosine diphosphate (ADP) and inorganic phosphate in enzymatic phosphate-group transfer reactions that are coupled to specific oxidation steps during catabolism. Since the ATP so formed can now diffuse to those sites in the cell where its energy is required, it is thus also a transport form of energy. The chemical energy of ATP is then released during transfer of its terminal phosphate groups to certain specific acceptor molecules, which become energized and can do work.

An advantage of the intraperitoneal administration of magnesium salts, methenamine or its salts, and dextrose provided by the invention, is that the toxic levels of magnesium and its associated adverse effects are avoided through intraperitoneal administration. Prior art methods of administration, such as IV (intra-venous) or IM (intra-muscle) injection, result in toxic levels of magnesium due to their rapid absorption by the body. As a result of the invention, the intraperitoneal administration allows the body to have the benefits of an abundance of magnesium that increases free energy and produces the therapeutic effect.

The instant invention provides several advantages. A principal advantage is that it plays a key role in providing free energy that allows the organism to act against the infectious and noninfectious inflammatory response. Numerous other advantages are provided by the invention. For example, a variety infectious and non-infectious inflammatory and inflammation-related diseases can usually be treated with a single treatment. In complicated cases, it typically requires only a second treatment, which is typically administered on the third day after the first treatment. Another advantage of the invention is that it can be used in treating multiple diseases simultaneously, since multiple diseases may simultaneously cause inflammation. For example, when treating an animal for mastitis, the animal may also have salpingitis. A solution embodying the invention can be used to simultaneously treat both of these diseases. After the treatment, the animal would get estrus on the seventh day after administration of the solution, and ninety percent of them would get pregnant after artificial insemination, except the time of parturation, when the uterus contracts to normal size (approximately 2–3 weeks).

It has been found that a pharmaceutical solution embodying the invention can be safely used in pregnant animals without adverse side effects for the mother and the fetus. Likewise, it has been found that it can also be successfully used for animals having a wide range of ages. In experimental use on cattle, miscarriages or intoxication were never encountered. In fact, within 10–15 minutes after administration of the solution all cows start rumination. It has been found in experimental use that upon injection of the solution, no problems with inflammation, irritation, infection and peritonitis were encountered. In fact, this invention has been effectively used for treatment of inflammation, infection and peritonitis.

Other advantages of the instant invention is that it can accelerate the process of recovering, raise the productivity of animal husbandry, facilitate the labor of the veterinarian doctors, simultaneously treat different diseases and to have a great therapeutic effect with one time intraperitoneal administration. When it is used for skin and wound infection, the invention does not require daily use of different antibiotics, cleaning of the infected area, applying antibacterial ointments, daily dressing changes, and removing of the necrotic tissue. Further, the invention does not require that the causative pathogen be isolated to determine its sensitivity to antibiotics. By eliminating the necessity to administer antibiotics, the invention also avoids the buildup of bacterial resistance to antibiotics. A number of different bacteria and fungi can be treated with the solution, including *Streptococcus, Staphylococus, Escherichia coli, Enterobacter aerogenes, Klebsiella, Clostridium perfringes, Pseudomonas aeruginosa, Corynebacterium pyogenes,* and *Candida albicans.*

Because inflammation occurs due to a wide variety of conditions, other advantages of the invention is that it proposes the use of intraperitoneal solution as an analgesic, antispasmatic and laxative, and that it decreases the reproductive failures and increases in fertility where other medications have failed to help.

An economic advantage of the invention is that the compositions used to produce the solution are inexpensive to manufacture. Therefore, due to its low-cost, the benefit of this invention can be distributed widely for the benefit of a large segment of the population. A detailed discussion of specific preferred embodiments of the invention now follows.

A preferred embodiment for treating inflammatory and inflammatory-related disorders in animals comprises intraperitoneal administration of the solution comprising an effective amount of magnesium salts ($MgSO_4 \times 7H_2O$), methenamine (hexamethylenetetramine, $C_6H_{12}N_4$) or its salts, and dextrose ($C_6H_{12}O_6 \cdot H_2O$). It has been found that approximately 40 grams of magnesium sulfate dissolved in distilled water, for a cow of 500 kg, administered by intraperitoneal injection, provides successful treatment of inflammatory disorders without any side effects. After several years of using magnesium salts, the dose was reduced to an average dose of 3–20 grams for a 500 kg cow to get the same therapeutic effect. Therefore, the intraperitoneal administration, compared to other methods of drug administration, is a safe method because it avoids the toxic side effects through first-pass hepatic metabolism which permits the organism to create the abundance of magnesium used for recovery and healing. In fact, the administered dose can be higher than the traditional toxic level doses.

In addition to the magnesium salt described above (magnesium sulfate), other magnesium salts may also be used with similar results. For example, the following salts may be substituted for magnesium sulfate ($MgSO_4 \times 7H_2O$): magnesium taurate ($(H_2NCH_2CH_2SO_3^-)_2Mg^{2+}$), magnesium chloride ($MgCl_2$, and $MgCl_2 \cdot 6H_2O$). As a result, those skilled in the art will realize that magnesium sulfate is only an example of several magnesium salts which may be effectively used by the invention.

Magnesium is the ingredient which allows the organism to generate energy, mainly involving in the hydrolysis as well as the synthesis of ATP, and it is the main cofactor to three hundred different reactions involving the transfer of the phosphate groups, and also is a key component in cellular replication, transcription and ribosome stabilization. The free energy provided by the present invention is useful for treatment of a variety of inflammatory-related disorders. For example, conditions such as physiological edema and congestion of the udder, atony of the rumen, reticulum and abamasum, dystocia, diarrhea, rumen impaction, grain overload, prevention of metritis after retained placenta, cesarean section and after ceasarian section, the uterine prolapse and eversion are all helped when the organism is assisted in reduction in inflammation by the magnesium provided by the invention. Also, the invention allows treatment of persistent corpus luteum and anophrodisia of the ovaries; for example, on the seventh day after intraperitoneal administration of the solution, cows that were not pregnant had estrus and were able to get pregnant after artificial insemination despite the time of the next estrus.

In addition to the foregoing, the anti-inflammatory benefits of the invention have been found to be useful as an analgesic, antispasmatic and laxative. For example, during calving of weak and strong contractions of the uterus, atony of the rumen, reticulum and abamasum, colic and constipation. In fact, after administration of the solution, the effect can be seen even in complicated cases when intoxication takes place, the temperature of the body is increased, and there is loss of appetite. In this situation, the cow starts to ruminate and the general condition improves in 10 to 15 minutes after administration of the solution. It was also found that after administration of magnesium, the general condition of the animal improved on the third day, and complete recovery was seen on the seventh day. The cows that previously did not have estrus, had estrus on the seventh day after administration and became pregnant after artificial insemination.

It has been found that the use of methenamine or its salts along with magnesium salts can accelerate the anti-inflammatory effect and process of recovering in complicated cases. Methenamine breaks down to formaldehyde and ammonia in areas of inflammation where formaldehyde acts as anti-inflammatory and bactericidal agent. Methenamine also increases membrane permeability, which helps to eliminate antibacterial toxic material from the body. When the dose of methenamine was increased to 20 grams per 500 kg, it allowed successful treatment of parturient paresis in cows (milk fever), ketosis (acetonomia), and paraplegia gravidarum when other therapies were unsuccessful. After the fifteen minutes of administration, the condition of cows that had parturient paresis (milk fever), ketosis (acetonomia) started to improve and the cows began rumination again.

A third ingredient, dextrose, was added to the composition to increase the function of the cells and tissues by providing free energy. Dextrose in combination with magnesium salts and methenamine or its salts, lowers their toxicity, increases their duration, and increases the antibacterial effect. Those skilled in the arts will recognize that while the magnesium will work without the other ingredients, the addition of methenamine and dextrose to the solution will result in a treatment which provides the synergetic effect.

In a preferred embodiment of the method of preparation of the magnesium salts, methenamine salts and dextrose solution for use in the treatment of cows that weigh approximately 500 kilograms, the following doses are used: magnesium sulfate is 3–20 grams, methenamine 2.5–30 grams, and dextrose 2.5–12.5 grams.

In this embodiment, the solution is produced by the following method: first, 3–20 grams of magnesium salts are dissolved in 230 ml of distilled water; then 2.5–12.5 grams of dextrose are added. Then the solution is sterilized at 100 degrees Celsius for 30 minutes. After sterilization, the solution is cooled to a temperature of 25–30 degrees Celsius. Once cooled, 2.5–30 grams of methenamine or its salts are added by antiseptic techniques. The volume of distilled water depends on the amount and concentration of the dissolved ingredients. The final volume of the solution should be approximately 250 ml. Sterile water can be added to bring the solution volume to this level. At this point, the solution is ready to be administered. The solution is administered intraperitoneally, at a temperature of 25–30 degrees Celsius. The 250 ml solution would be used for each 500 kilograms of body weight. The exact amount administered would be based on this 500KG/250 ml W/V ratio. Those skilled in the art will recognize that the distilled water solution can be replaced with a saline solution, typically 0.1% to 0.9%, or a Ringer's solution (Ringer's solution is well known in the art).

Those skilled in the arts will recognize that it is possible to provide magnesium to living organisms with different magnesium based solutions to create an abundance of magnesium to create free energy. As mentioned above, a variety of magnesium salts may be used, including $MgSO_4 \times 7H_2O$, $(H_2NCH_2CH_2SO_3^-)_2Mg^{2+}$, $MgCl_2$, and $MgCl_2$ 6H2O. For example, an alternative preferred embodiment provides a magnesium based solutions made from magnesium sulfate, magnesium chlorate, magnesium heptahydrate, magnesium taurate, and Epson salts. Likewise, the dextrose used in the preferred embodiment can be replaced with glucose. Yet another alternative preferred embodiment provides a solution which includes methenamine, or hexamethylenetetramine, and its salts: methenamine hippurate and methenamine mandelate. A further preferred embodiment provides a solution which includes methenamine salt, s methenamine hippurate, and methenamine mandelate from 1% to 16% W/V.

When used with animals, solution is preferably administered on the right side of the animal's body (in cows and sheep) in the paralumbar fossa (however, in horses it is administered on the left side). Of course, the injection site is prepared by using antiseptic techniques: cutting out the hair and using the alcohol and the iodine solution to prepare the site of injection. The results of the administration of the solution do not depend on the rate of infusion. An A-20×40 12U-M3 needle can be used for injection. Those skilled in the art will recognize that any suitable needle size can be selected depending on the nature of the organism being injected. The needle is then connected via the connector to the bottle with the prepared solution, and the solution is administered. In addition, the solution can also be effective if injected subcutaneously.

The solution can be administered every day without any side effect. However, the therapeutic effect can be achieved with a single administration in most cases, and in complicated cases, the solution can be administered again on the third day after the first administration to achieve adequate results. Examples of the inflammatory diseases commonly encountered in the veterinary practice that can be treated by the present invention are mastitis, vaginitis, cervicitis, salpingitis, metritis, endometritis, pyometra, retained placenta, wound infection, dermatitis, eczema, decubitus ulcers, osteomyelitis, gastroenteritis, colitis, and diarrhea. The reason why this single preparation is useful for the treatment of a wide variety of conditions is that it treats the condition by facilitating the organism's natural healing ability to deal with inflammation which may have been caused by any number of the foregoing maladies. This is accomplished by the intraperitoneal solution which provides the abundance of magnesium required by the healing process.

Those skilled then the arts will recognize that due to its ability to assist organisms at the cellular level to act against inflammation, the present invention provides an opportunity to treat other different diseases in both human, veterinary and possibly in an allopathic medicine. For example, meningitis, encephalitis, hepatitis, pancreatitis (acute and chronic), irritable bowel syndrome, infections of biliary system, vitamin deficiencies, bronchitis, asthma, diabetes, Chronic Obstructive Pulmonary Disease (COPD), pneumonians, psoriases, Inflamatory Bowel Disease (IBD)—Crohn disease (CD), and ulcerative colitis (UC) all may be affected by inflammation. As a result, all of these widely different diseases may be helped by a single medication which is designed to treat a common aspect of those diseases, namely inflammation.

Inflammation is not limited to internal organs. Therefore, those skilled in the arts will recognize that it can also be used for treatment of a variety of inflammatory disorders of the skin. For example, it is possible to use this invention for treatment of the skin infected with smallpox and anthrax because it assists the organism in reducing the inflammation produced by these respective diseases. Of course, some diseases, such as HIV and cancer can cause inflammation in a wide variety of locations within an organism. It is therefore possible to use this invention in the treatment of HIV and cancer symptoms.

Two more clearly illustrate how the invention can be used in different situations, the following detailed examples of the present invention. Those skilled in the arts will recognize that these examples are not intended to limit the number of uses of the invention, but are merely illustrative in nature. This invention can be used to treat any mammal, including humans, who have a condition which is affected by inflammation.

EXAMPLE 1

Parturition

During calving, problems can occur in cases of strong and weak contractions. After the solution is administered, the cervix of the uterus will relax and the calving will proceed without complications. In all the cases, the placenta should separate on its own. A distinct advantage of the invention in this case is that the solution results in a reduction in inflammation after calving that allows a substantial percentage of cows, approximately 90%, to enter estrus during the first month. This permits artificial insemination to be performed earlier than normal, which results in more economically productive use of the cows.

EXAMPLE 2

Cervicitis and Vaginitis

During calving, rapture of the cervix in young cows is often seen when a large calf is delivered. This condition can be complicated by cervicitis and vaginitis. The most consistent clinical sign is vaginal discharge that may be serous, serosanguineous or mucopurelent. In the complicated cases phlegmone paravaginalis can develop. It has been found that when these conditions occur, after the first administration of the solution, substantial improvement in the condition of the cows was seen. In particular, approximately 80% of the cows developed estrus and were able to become pregnant in the first month. While the remaining 20% of the cows improved their condition, they did not develop estrus. However, after a second administration of the solution, the remaining 20% of the cows developed estrus shortly thereafter and were able to become pregnant after artificial insemination.

EXAMPLE 3

Retained Placenta

If fetal membranes are not expelled within 12–24 hours after calving, membranes are considered to be retained. Membrane retention can cause problems for the cow and needs to be addressed quickly. The solution should be administered to cows where the expulsion of the fetal membranes did not occur within 6–24 hours. It has been found that in approximately 60% of cases, the expulsion of fetal membranes takes place after the solution is introduced. In the remaining 40% of cases, the expulsion of the fetal membranes did not take place within 24 hours after administration of the solution. While the placenta must be removed manually; in these cases the manual removal is typically very easy due to the reduced inflammation. It is preferred that on the third day after the first administration of the solution, a second dose the given to prevent the development of metritis. If metritis occurs, it is treated in the same manner. It is been found that in 90% of these cases, estrus is seen in the first month after calving, and the treated cows became pregnant after artificial insemination. The solution was introduced again to the rest of the cows (10%), and on the seventh day they developed estrus and got pregnant after artificial insemination.

EXAMPLE 4

Uterine Prolapse and Eversion

The prolapse of the uterus usually occurs within a few hours after calving. During the uterine prolapse, if the placenta is present, it is separated and then the uterus is returned to its normal position. After this event, the solution is administered. Typically, a majority of these cases are complicated by metritis. It has been found that if the solution is used, the course of metritis is not complicated and the recovery is successful due to a reduction in inflammation which is a contributing factor in the aforementioned complications. In complicated cases, the solution can be used again shortly thereafter. In this and the other examples provided herein, the second administration of the solution is preferably given on the third day. However, those skilled in the art will recognize that the exact timing of the second administration is not critical, and it can be administered earlier or later. Typically, treated cows have estrus during the first month after calving. This is due to be accelerated recovery of the organism caused by the reduction of swelling. It has been found that a high percentage, approximately 75% of the cows that undergo treatment are able to become pregnant by artificial insemination. About 15% of the remaining cows may require a second injection, after which estrus occurs shortly thereafter, in approximately seven days. About 10% of cows could not be successfully inseminated. As can be seen, the accelerated reduction in inflammation provided by the solution allows accelerated recovery of the animal who can more quickly be inseminated and get pregnant.

EXAMPLE 5

Metritis and Endometritis

The solution has also been used to successfully treat all kind of metritis and endometritis. On the third day of pathological calving, after the removal of the placenta, during the cause of acute pathological mastitis the uterus would have the exudative fetid discharge of brownish-black color. Sometimes, several gallons of fluid may accumulate in the uterus. After administration of the solution, during the twenty-four hour period, the condition of the animal has been found to dramatically improve, and on the third day the fetid discharge has been observed to disappear completely which guarantees a high success rate measured at 96%.

After treatment, the metritis turns into fibrinous one, which lasts for three days, the discharge then exhibits a thick, red-brown color. Then, the metritis turns into a purulent metritis with a thick, light-yellow color of the discharge. Every day, the discharge changes its color to more lighter one, and finally the discharge stops, and the animals become healthy. After the calving (about 30–35 days), all the cows that were treated had estrus and 90% of them became pregnant after artificial insemination. In complicated cases of metritis, the injection needed to be administered a second time.

EXAMPLE 6

Persistent Corpus of Luteum, Anaphrodisia of the Ovaries, Nyphomania, Follicular Cysts After the use of the solution in cases of follicular cysts and persistent corpus luteum for the cows that did not get estrus after the first injection, on the seventh day the solution was given again. In all of the cases, an 80% success rate was observed. During the treatment of anaphrodisia and nyphomania, the injection had to be repeated on the third day. Seventy-five percent of these cows had estrus and were able to be inseminated.

EXAMPLE 7

Mastitis (Peracute, Acute, Coliform, Subacute, Subclinical)

Mastitis is fairly common, and can arise from a variety of causes. One type of mastitis can develop during lactation. The solution has been found to be very effective in treating mastitis in addition to the other forms. Sometimes, during the six hours after administration of the solution, the quantity of milk decreases, thereby allowing the recovery period to take place faster. Eighty-five percent of the animals were observed to recover on the third day, the rest 15% had to be given the repeated injection. Out of 15%, about 5% recovered on the third day after the second injection. The cows that were treated with mastitis that had underlying infertility disorders were able to get estrus on the seventh day after administration and get pregnant after artificial insemination. In the case of peracute and acute form of mastitis, when the systemic disturbance is seen such as fever, weakness, and anorexia, after the injection was given, the animal was able to ruminate in about 10–15 minutes, and the general conditions start to improve.

EXAMPLE 8

Physiological Edema and Congestion of the Udder

This condition occurs in the first-calf heifers prior to and after calving in high-producing dairy cattle. The udder in these cases is very large, hard and free of mastitis. After the first injection, the udder becomes soft and on the third day it becomes normal, also these animals had estrus and were able to become pregnant earlier than those cows that did not have any complications. In complicating cases, the injection was given again on the third day after the first injection. All the cows that underwent this treatment were treated with a 95% success, and had estrus during the first month, and became pregnant after artificial insemination.

EXAMPLE 9

Rumen Impaction

Grain overload (Rumen impaction) is the acute disease of ruminants characterized by indigestion, dehydration, acidosis, toxemia, collapse and frequently death. The solution has been found to be effective in the treatment of this condition if it is diagnosed early, for example, within 8 hours of onset. Within 10–15 minutes after the solution is given, a substantial portion (approximately 80%) of cows are able to start rumination again. The other 15% of cows have been observed to improve, and they required the second injection to become free of illness. In the case of atony of the rumen, and abomasal, 95% of cows would start to ruminate again within 10–15 minutes after the injection was given.

EXAMPLE 10

Enteritis (Gastroenteritis and Enterocolitis)

The above conditions are usually accompanied by weakness, decreased rumination, and diarrhea with different stool color sometimes bloody, foul-smelling, increased temperature, and vomiting in swine. The abdomen is tense in acute cases and the animal develops pain when it is palpated. Regardless of the pathogens involved in the above conditions, the reduction in inflammation provided by the solution allowed these cases to be treated very successfully. It was found that after the first injection, during the 24-hour period, the general condition improves, the diarrhea ceases, and on the third day, the animal gets healthy. Those animals (20%) that did not improve completely required second injection, and on the seventh day 90% of these animals became healthy.

EXAMPLE 11

Bloat in Ruminants (Tympany, Meteorism)

Tympany is an excessive accumulation of gas in the rumen and reticulum of the ruminant stomach. This is commonly seen in cattle. Because of the clinical presentation, accumulation of air throughout the peritoneal cavity, it was difficult to administer the solution. In fact, if the injection is introduced, there was 90% therapeutic effect after 10–15 minutes. Sometimes, trocarizatition of the rumen is required in the treatment of the tympany. One of the complications of this procedure is peritonitis, which is usually seen within 6 hours of trocarization. In these cases, the solution is used twice, on the first and the third day, with approximately 90% success because the solution was introduced into the peritoneum. It can be concluded that this medication can be used for prevention and treatment of peritonitis, after the primary cause is eliminated. Also, great success was found in the treatment of peritonitis induced by the inflammation of the umbilical cord of the newly born animals, in this condition two injections of the solution were required.

EXAMPLE 12

After incision ans drainage of wound Infections (Including Lower Extremities and Phalanges), Laminites, Foot Rot, Abscess, Phlegmons, and Traumas of Different Body Areas, it has been found that after the elimination of the cause and after the use of the solution, the general condition of the animal improves more rapidly due to the reduction in inflammation. Typically, only a single injection is required. The wound infections, even those with foul smell, have been successfully treated with the solution, and did not require any wound care including bandages and antibacterial ointments.

EXAMPLE 13

Skin Disorders Such as Dermatitis (in Different Body Areas), Eczemas, Decubitus (Pressure) Ulcers It has been found that the elimination of the cause and changing the animal position if they are weak, the use of the solution improves the general condition of animals by contributing to the elimination of inflammation. In complicated cases, the solution should be administered again. Two injections were usually required to achieve therapeutic effect. On the seventh day, after the second injection, the condition of the animals improve.

Analyzing the above testing, it has been found that the solution provided by this invention can be used in a wide variety of treatments related to illnesses and injuries suffered by any mammal, including humans. The advantages and benefits provided by the invention are the result of a specific combination of materials which assist body, and accelerate its ability, in the natural process of producing inflammation.

While the invention has been described with respect to a preferred embodiment thereof, it will be understood by those skilled in the art that various changes in detail may be made therein without departing from the spirit, scope, and teaching of the invention. For example, the solution strength may be anything suitable for the particular organism being treated, the manner of application can vary, etc. Accordingly, the invention herein disclosed is to be limited only as specified in the following claims.

We claim:

1. A method of treating inflammation in mammals by intraperitoneally administering substantial amounts of magnesium salts into the intraperitoneal cavity for absorption by the mammal to accelerate the natural healing process in the mammal, including the steps of:

forming a solution which contains magnesium salts in a range of approximately 1.2% to 12% W/V; and intraperitoneally administering an amount of the solution to a mammal in need of treatment for inflammation, so that the magnesium is absorbed into the mammal via the intraperitoneal cavity in substantial quantities (i) which would be toxic for that mammal's body weight if administered via intravenous or intramuscular injection, and (ii) which are effective to raise the level of magnesium in the mammal's body to a higher than normal level of magnesium, wherein said higher than normal level of magnesium is utilized by the mammal to produce increased levels of adenosine triphosphate which carry chemical energy throughout the mammal's body and which is used in the normal cellular level process of reducing inflammation;

whereby the reduction of inflammation in the treated mammal is accelerated by absorption via the intraperitoneal said of substantial quantities of magnesium salts into the mammal which in turn raises the magnesium level in the body to a higher than normal level.

2. A method, as in claim 1, including the additional step of adding methenamine, methenamine hippurate, or methenamine mandelate, to the solution.

3. A method, as in claim 2, wherein the methenamine, methenamine hippurate, or methenamine mandelate is added in a range of approximately 1% to 12% W/V to the solution.

4. A method, as in claim 3, including the additional step of adding dextrose to the solution.

5. A method, as in claim 4, wherein the dextrose is added in a range of approximately 1% to 5% WN to the solution.

6. A method, as in claim 3, including the additional steps of:
preparing the solution for each 500 kilograms of body weight in the following proportions:
dissolving approximately 3–20 grams of magnesium salts in approximately 230 ml of solution;
adding approximately 2.5–12.5 grams of dextrose;
sterilizing the solution;
cooling the solution to a temperature of approximately 25–30 degrees Celsius;
adding approximately 2.5–30 grams of methenamine salts; and adding sterile water to bring the total solution volume to approximately 250 ml.

7. A method, as in claim 6, including the additional step of sterilizing the solution by heating it to approximately 100 degrees Celsius for approximately 30 minutes.

8. A method, as in claim 1, including the additional step of adding dextrose to the solution.

9. A method, as in claim 8, wherein dextrose is added in a range of approximately 1% to 5% W/V to the solution.

10. A method, as in claim 1, including the additional step of using distilled water as the solvent of the solution.

11. A method, as in claim 10, including the additional step of adding methenamine, methenamine hippurate, or methenamine mandelate, in a range of approximately 1% to 12% W/V to the solution.

12. A method, as in claim 11, including the additional step of adding dextrose to the solution.

13. A method, as in claim 12, wherein the dextrose is added in a range of approximately 1% to 5% W/V to the solution.

14. A method, as in claim 10, including the additional step of adding dextrose in a range of approximately 1% to 5% W/V to the solution.

15. A method, as in claim 1, including the additional step of using a saline solution as the solvent of the solution.

16. A method, as in claim 15, wherein the saline solution is 0.1 to 0.9% W/V sodium chloride.

17. A method, as in claim 15, including the additional step of adding dextrose in a range of approximately 1% to 5% W/V to the solution.

18. A method, as in claim 1, wherein the magnesium salt is magnesium sulfate, magnesium sulfate heptahydrate, or epsom salts.

19. A method, as in claim 1, wherein the solution is obtained by adding a sufficient amount of magnesium salts to a Ringer's solution.

20. A method, as in claim 1, wherein the magnesium salt is $MgCl_2$, or $MgCl_2.6H_2O$.

21. A method of treating inflammation in mammals by intraperitoneally administering substantial amounts of magnesium salts into the intraperitoneal cavity for absorption by the mammal to accelerate the natural healing process in the mammal, including the steps of:
forming a solution which contains magnesium salts in a range of approximately 1.2% to 12% WN and methenamine or its salts in a range of approximately 1% to 12% W/V; and
intraperitoneally administering the solution to a mammal in need of treatment for inflammation, so that the magnesium is absorbed into the mammal via the intraperitoneal cavity insubstantial quantities (i) which would beloxic for that mammal's body weight if administered via intravenous or intramuscular injection, and (ii) which are effective to raise the level of magnesium in the mammal's body to a higher than normal level of magnesium, wherein said higher than normal level of magnesium is utilized by the mammal to produce increased levels of adenosine triphosphate which is used in the normal cellular level process of reducing inflammation;
whereby the reduction of inflammation is accelerated by absorption via the intraperitoneal cavity of said substantial quantities of magnesium salts into the mammal which in turn raises the magnesium level in the body to a higher than normal level.

22. A method, as in claim 21, including the additional step of adding dextrose in a range of approximately 1% to 5% W/V to the solution.

23. A method, as in claim 21, wherein the methenamine salts are methenamine hippurate or methenamine mandelate in a range of approximately 1% to 12% W/V to the solution.

* * * * *